US012749179B2

(12) United States Patent
Dahdouh

(10) Patent No.: US 12,749,179 B2
(45) Date of Patent: Sep. 29, 2026

(54) MEDICAL IMAGE AUGMENTATION

(71) Applicant: Canon Kabushiki Kaisha, Tokyo (JP)

(72) Inventor: Sonia Dahdouh, Edinburgh (GB)

(73) Assignee: Canon Kabushiki Kaisha, Tokyo (JP)

( * ) Notice: Subject to any disclaimer, the term of this patent is extended or adjusted under 35 U.S.C. 154(b) by 571 days.

(21) Appl. No.: 18/051,284

(22) Filed: Oct. 31, 2022

(65) Prior Publication Data

US 2024/0144472 A1 May 2, 2024

(51) Int. Cl.

| | |
|---|---|
| ***G06T 7/00*** | (2017.01) |
| ***G06F 18/214*** | (2023.01) |
| ***G06T 5/77*** | (2024.01) |
| ***G06T 7/33*** | (2017.01) |
| ***G06T 7/73*** | (2017.01) |
| ***G06T 11/00*** | (2026.01) |
| ***G06V 10/774*** | (2022.01) |
| ***G16H 30/40*** | (2018.01) |

(52) U.S. Cl.

CPC .......... *G06T 7/0012* (2013.01); *G06F 18/214* (2023.01); *G06T 5/77* (2024.01); *G06T 7/337* (2017.01); *G06T 7/74* (2017.01); *G06T 11/00* (2013.01); *G06V 10/774* (2022.01); *G16H 30/40* (2018.01); *G06T 2207/30096* (2013.01)

(58) Field of Classification Search

CPC .. G06T 7/521; G06T 7/55; G06T 7/13; G06T 7/74; G06T 7/11; G06T 7/0012; G06T 5/77; G06T 3/00; G06T 2207/10028; G06T 2207/10024; G06T 2207/20081; G06T 2207/30096; G06T 7/337; G06T 11/00; G16H 50/70; G16H 30/40; G06V 10/25; G06V 10/774; G06V 2201/03; G06F 18/214

See application file for complete search history.

(56) References Cited

U.S. PATENT DOCUMENTS

2011/0216951 A1 9/2011 Ye et al.
2014/0212014 A1* 7/2014 Kim .......................... G06T 3/14
382/131

(Continued)

FOREIGN PATENT DOCUMENTS

WO WO 2021/260396 A1 12/2021

OTHER PUBLICATIONS

F. Xing, X. Liu, C. . -C. J. Kuo, G. E. Fakhri and J. Woo, "Brain MR Atlas Construction Using Symmetric Deep Neural Inpainting," in IEEE Journal of Biomedical and Health Informatics, vol. 26, No. 7, pp. 3185-3196, Jul. 2022, doi: 10.1109/JBHI.2022.3149754. (Year: 2022).*

(Continued)

*Primary Examiner* — Sumati Lefkowitz
*Assistant Examiner* — Ryan P Potts
(74) *Attorney, Agent, or Firm* — Oblon, McClelland, Maier & Neustadt, L.L.P.

(57) ABSTRACT

A medical imaging system includes a data storage resource to store probability data representing probability information for a location of a feature of interest in an anatomical region. The system further includes processing circuitry to receive medical image data representing a medical image of the anatomical region, retrieve the probability data from the data storage resource, process the medical image data to perform an image augmentation operation on the received medical image for a feature of interest based on the probability information for the location of the feature of interest in the anatomical region.

18 Claims, 5 Drawing Sheets

(56) References Cited

U.S. PATENT DOCUMENTS

| | | | | |
|---|---|---|---|---|
| 2015/0045651 | A1* | 2/2015 | Crainiceanu | G01R 33/385 600/410 |
| 2021/0295966 | A1 | 9/2021 | Lyman et al. | |
| 2021/0327054 | A1* | 10/2021 | Liu | G06T 7/11 |
| 2022/0012877 | A1 | 1/2022 | Buckler et al. | |
| 2022/0167947 | A1* | 6/2022 | Seth | G06N 20/00 |
| 2022/0301163 | A1* | 9/2022 | C. | G06N 20/00 |
| 2024/0062523 | A1* | 2/2024 | Zhao | G16H 50/50 |

OTHER PUBLICATIONS

Pezeshk, Aria, et al. "Seamless lesion insertion for data augmentation in CAD training." IEEE transactions on medical imaging 36.4 (2016): 1005-1015. (Year: 2016).*

Dwibedi, D. et al. "Cut, Paste and Learn: Surprisingly Easy Synthesis for Instance Detection" arXiv:1708.01642v1 [cs.CV] Aug. 4, 2017. (11 pages).

Fang, H. et al. "InstaBoost: Boosting Instance Segmentation via Probability Map Guided Copy-Pasting" arXiv:1908.07801v1 [cs.CV] Aug. 21, 2019. (10 pages).

Ghiasi, G. et al. "Simple Copy-Paste is a Strong Data Augmentation Method for Instance Segmentation" arXiv:2012.07177v2 [cs.CV] Jun. 23, 2021 (13 pages).

Yang, J. et al. "TumorCP: A Simple but Effective Object-Level Data Augmentation for Tumor Segmentation" arXiv:2107.09843v1 [cs.CV] Jul. 21, 2021 (10 pages).

Dai, P. et al. "Soft-CP: A Credible and Effective Data Augmentation for Semantic Segmentation of Medical Lesions" arxiv, 2022 (9 pages).

* cited by examiner

MEDICAL IMAGE AUGMENTATION

FIELD

Embodiments described herein relate generally to a method and apparatus for performing an image augmentation process on medical image data.

BACKGROUND

Medical image data, obtained using a variety of imaging modalities may be used for a wide variety of diagnostic, treatment or other purposes. It is known to train machine-learning procedures, for example, convolutional neural network based procedures, on medical image data, and to use such trained machine learning procedures for a wide variety of tasks or purposes.

Machine learning models, such as deep learning models based on convolutional neural networks, may require large annotated datasets for the purposes of training the network. Production of high-quality annotated datasets for the purposes of training may require a large amount of labour and/or specific domain knowledge, in particular, in specialized fields such as medical imaging. In such fields, it may be difficult to obtain sufficiently large datasets for the purposes of training a machine learning procedure.

SUMMARY

In a first aspect, there is provided a medical imaging system comprising: a data storage resource configured to store probability data representing probability information for a location of a feature of interest in an anatomical region; processing circuitry configured to: receive medical image data representing a medical image of at least an anatomical region; retrieve the probability data from the data storage resource; process the medical image data to perform at least one image augmentation operation on the received medical image for at least one feature of interest based on the probability information for the location of the at least one feature of interest in the anatomical region.

The processing circuitry may be configured to determine an augmentation position in the medical image based on the probability information for the location and the augmentation operation comprises adding the feature of interest to the image at the augmentation position.

The augmentation operation may further comprise performing an image blending process, for example an inpainting process, for the feature of interest at the determined augmentation position.

The at least one augmentation operation may comprise removing a feature of interest from the received medical image to form a removed patch and performing an image data reconstruction process on the removed patch using image data obtained from a further patch of the received medical image and/or a patch of a reference image.

The patch of the received medical image and/or reference image may be selected based on a spatial relationship between the removed patch and the patch and/or is based on symmetry information for the anatomical region.

The feature of interest may comprise at least one of a lesion, pathology or artefact.

The probability information for the location may be represented by a probability map. The probability information may be representative of a spatial probability density across the anatomical region. The probability information may be representative of anatomical information and/or anatomical knowledge of the feature of interest in the anatomical region.

The method may further comprise determining a further augmentation feature parameter for the feature of interest, wherein the further augmentation feature parameter comprises at least one of: size and/or scale and/or type and/or subtype, optionally wherein the further augmentation feature parameter is selected using probability information associated with that parameter.

The processing circuitry may be further configured to: obtain reference image data representing one or more images of at least a part of the anatomical region; determine a geometrical mapping between the part of the anatomical region and a corresponding part of the received medical image; and wherein the at least one augmentation operation is based at least one on the determined geometrical mapping.

The reference image data may represent one or more anatomical atlases. The reference image data may represent one or more further reference images in the same modality. The reference image data may comprises a tissue volume or a set of tissue volumes. The reference image data may be representative of a part of the anatomical region free of the feature of interest.

The at least one augmentation operation may comprise adding one or more features of interest to the received image and/or removing one or more features of interest from the received image.

The processing circuitry may be further configured to obtain image data representative of the feature of interest and perform a transformation on the obtained image data to produce a transformed feature of interest for augmenting to the medical image.

The at least one augmentation operation may further comprise an image data reconstruction process and/or image blending process, wherein the image data reconstruction process and/or image blending process is performed in accordance with a pre-determined image data reconstruction and/or image blending procedure, selected based on at least one of a modality and/or a type of the feature of interest and/or an anatomical location.

The pre-determined procedure may comprise a procedure based on local blending, for example, a Poisson blending and/or other inpainting procedure.

The processing circuitry may be configured to perform a transformation of the received medical image based on a manual, rigid or non-rigid registration or any combination thereof, and/or based on a plurality of landmarks.

The at least one augmentation operation may comprise applying one or more distortions to the feature of interest. The one or more distortions may comprise any combination of geometrical distortions and/or appearance distortions and/or wherein the one or more distortions is based on at least the anatomical region, one or more properties of the received image, the type and/or a further property of the feature of interest.

The processing circuitry may be further configured to determine probability information for location by processing medical image data representing a plurality of medical images of the anatomical region, wherein at least one of the plurality of medical images comprise the feature of interest in the anatomical region.

The method may further comprise obtaining annotation data for the received image associated with the feature of interest.

According to a further aspect, there is provided a method of augmenting an image comprising: receiving medical image data representing a medical image of at least an anatomical region; retrieving probability data from a data storage circuitry, wherein the probability data is representative of probability information for a location of a feature of interest in an anatomical region; processing the medical image data to perform at least one image augmentation operation on the received medical image for at least one feature of interest based on the probability information for the location of the at least one feature of interest in the anatomical region.

According to a further aspect there is provided a computer program product comprising computer-readable instructions that are executable to: receive medical image data representing a medical image of at least an anatomical region; retrieve probability data from the data storage circuitry, wherein the probability data is representative of probability information for a location of a feature of interest in an anatomical region; process the medical image data to perform at least one image augmentation operation on the received medical image for at least one feature of interest based on the probability information for the location of the at least one feature of interest in the anatomical region.

In a further aspect, there is provided a medical image processing apparatus comprising: a storage which stores a rule based on anatomical information, and processing circuitry configured to: receive medical image data for data augmentation, generate training data by processing data augmentation processing to the medical image data based on the rule.

The processing circuitry may be further configured to: receive image patch including a predetermined image characteristic, determine an inpainting position of the image patch within the medical image data based on the rule, generate the training data by inpainting the image patch on the inpainting position.

The processing circuitry may be further configured to: receive healthy medical image patch based on healthy medical image, determine an image region for removal within the medical image data based on the rule, generate the training data by inpainting the image region for removal to the healthy medical image patch.

The rule may comprise a positional probability map based on the anatomical information.

The positional probability map may comprise an atlas mapped an existence probability of a predetermined lesion.

The processing circuitry may be further configured to conduct a registration of the atlas and the medical image data.

In a further aspect, there is provided a medical imaging method comprising:

a) one or more medical images to be augmented;
b) one or more location probability density maps;
c) one or more augmentation features (lesions, pertinent features, or artefacts of interest);
d) one or more exemplar images, free of the features of interest listed in c);
e) determine geometrical mappings between corresponding tissues in the images to be augmented a) and the exemplar images d);
f) operations to perform on the images to be augmented a) within the list of adding one or more features of interest c), removing one or more features of interest c) or any combination of both;
g) determine locations in the exemplar images d) to insert relevant features c), where the location is calculated based on a spatial probability distribution b);
h) one or more distortions to be applied to the features of interest c);
i) positioning of the features of interest c) on the exemplar images d) according to exemplar anatomy;
j) determine a geometrical mapping between corresponding tissues in the exemplar images d) and the images to be augmented a);
k) apply the geometrical mapping j) to transfer the chosen augmentation feature c) into a plausible position in the image to be augmented a);
l) insert transformed augmentation feature k) into image to be augmented a).

The plurality of exemplar tissues that does not contain the lesions of interest may comprise anatomical atlas(es) in the same modality.

The plurality of exemplar tissues that does not contain the lesions of interest may comprise any tissue volume chosen as reference.

The plurality of exemplar tissues that does not contain the lesions of interest may comprise any set of tissue volumes chosen as reference.

The alignment of the anatomy of the tissue to be augmented may be aligned by any manual, rigid or non-rigid registration or any combination of these.

The alignment of the anatomy of the tissue to be augmented may be any alignment using manual or automated anatomical landmark points.

The features of interest c) distortions may be any combination of geometrical distortions and/or appearance distortions.

The augmentation feature positioning according to exemplar anatomy may be global positioning according to the spatial probability distribution.

The global positioning according to the spatial probability distribution may be combined with adjustment to the local anatomy using either manual, rigid, or non-rigid registration or any combination of these.

The alignment of the exemplar anatomy to the tissue to be augmented may be any manual, rigid or non-rigid registration or combination of any of these.

The method to insert transformed augmentation feature k) into image to be augmented a) may be any form of inpainting.

The choice of the operations to perform on augmentation features can be adding augmentation features c), removing them, or any combination of both.

The choice of the operation to perform on augmentation features may be addition and augmentation features c) may overlap, not overlap or any combination of both.

The choice of operation may be removal and the augmentation features c) removal choice may be random, according to a chosen type, according to a location, manually chosen or any combination of the above.

The inpainting of the removed augmentation features c) may be done using information coming from the symmetrical part of the tissue represented in the medical images a) if said symmetry exists and is relevant, information coming from the exemplar images or any combination of the above.

The choice of operation may be removal and the inpainting method used where the augmentation features c) may be any form of inpainting.

In a further aspect, there is provided a processing circuitry configured to:

receive a medical image to be augmented;
access a location probability density map representing probability of position or other property of a feature(s) of interest;

augment the medical image with the feature(s) of interest based on the probability density map.

The feature(s) of interest may comprise at least one of a lesion, pathology or artefact.

The processing circuitry may be further configured to: access one or more example images that, optionally, are free of the augmentation feature(s); determine a geometrical mapping between corresponding tissues in the image to be augmented and the example image(s); perform an operation on the image to be augmented comprising at least one of adding one or more features of interest or removing one or more features of interest, wherein the operation is performed at a selected position determined based on the geometrical mapping.

The example image(s) may comprise anatomical atlas(es) in the same modality.

The example image(s) may comprise a tissue volume, or set of tissue volumes, selected as a reference.

The processing circuitry may be configured to perform a transformation of the image to be augmented based on a manual, rigid or non-rigid registration or any combination thereof, and/or based on a plurality of landmarks.

The processing circuitry may be configured to apply a distortion(s) to the feature(s) of interest, optionally wherein the distortion(s) comprise any combination of geometrical distortions and/or appearance distortions.

BRIEF DESCRIPTION OF THE DRAWINGS

Embodiments are now described, by way of non-limiting example, and are illustrated in the following figures, in which.

DETAILED DESCRIPTION

Figure 1:
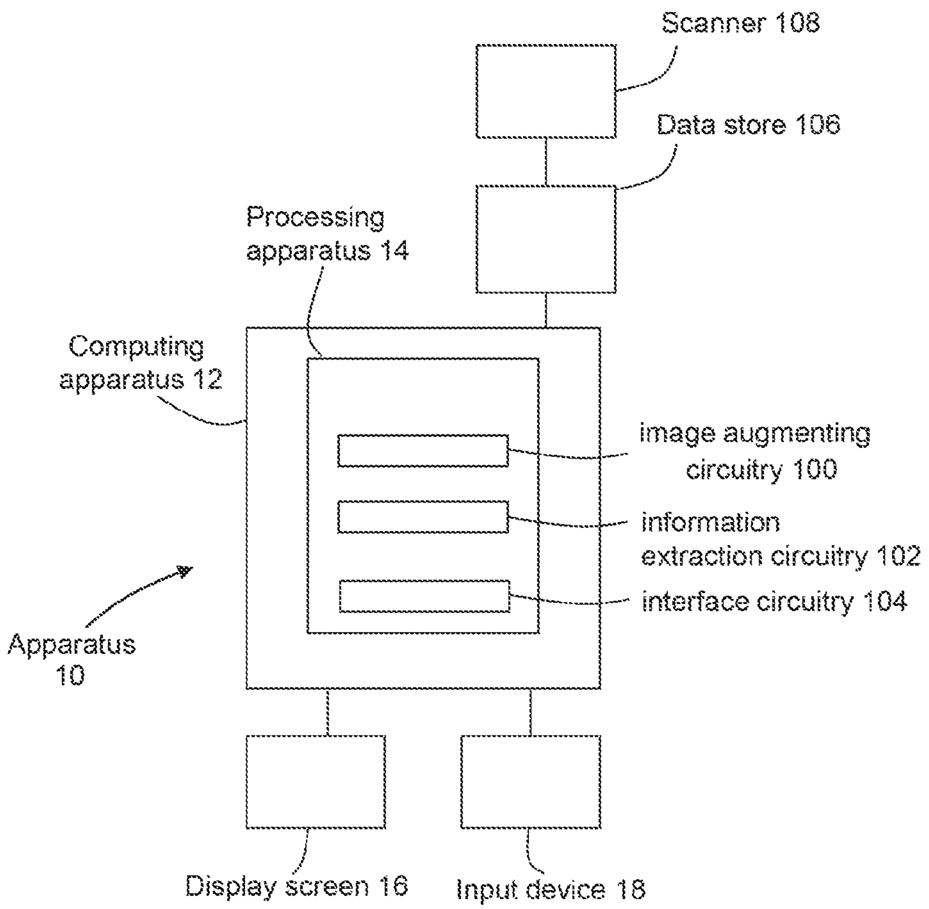
FIG. 1 is a schematic illustration of an apparatus in accordance with an embodiment.

A data processing apparatus 10 according to an embodiment is illustrated schematically in FIG. 1. In the present embodiment, the data processing apparatus 10 is configured to process medical imaging data. In other embodiments, the data processing apparatus 10 may be configured to process any other appropriate data.

The data processing apparatus 10 comprises a computing apparatus 12, which in this case is a personal computer (PC) or workstation. The computing apparatus 12 is connected to a display screen 16 or other display device, and an input device or devices 18, such as a computer keyboard and mouse. While FIG. 1 depicts a data processing apparatus with a personal computer or workstation, it will be understood that, in some embodiments, the data processing apparatus is a distributed computing apparatus, for example, including networked computing resources configured to perform one or more of the processing steps described in the following. In some embodiments, the data processing apparatus is implemented or forms part of a cloud based system.

The computing apparatus 12 is configured to obtain image data sets from a data store 106. The image data sets have been generated by processing data acquired by a scanner 108 and stored in the data store 106.

The scanner 108 is configured to generate medical imaging data, which may comprise two-, three- or four-dimensional data in any imaging modality. For example, the scanner 108 may comprise a magnetic resonance (MR or MRI) scanner, CT (computed tomography) scanner, cone-beam CT scanner, X-ray scanner, ultrasound scanner, PET (positron emission tomography) scanner or SPECT (single photon emission computed tomography) scanner. The medical imaging data may comprise or be associated with additional conditioning data, which may for example comprise non-imaging data.

The computing apparatus 12 may receive medical image data or other data from one or more further data stores (not shown) instead of or in addition to data store 106. For example, the computing apparatus 12 may receive medical image data from one or more remote data stores (not shown) which may form part of a Picture Archiving and Communication System (PACS) or other information system.

As described in the following embodiments, probability information, represented by probability data, is stored, on data store 106. Further data for the features of interest, for example, the lesion bank, are also stored on data store. In some embodiments, it will be understood that the probability data and the lesion data store are stored separately (for example, on different storage resources and/or at different storage locations connected to a network).

Computing apparatus 12 provides a processing circuitry or resource for automatically or semi-automatically processing medical image data. Computing apparatus 12 comprises a processing apparatus 14. The processing apparatus 14 comprises: image augmentation circuitry 100 configured to perform one or more augmentation operations on received medical image data; information extraction circuitry 102 configured to extract information, for example, location probability information, for one or more features of interest by processing medical image data representing a plurality of images of a feature of interest; and interface circuitry 104 configured to obtain user or other inputs and/or to output results of the data processing.

In the present embodiment, the circuitries 100, 102, 104 are each implemented in computing apparatus 12 by means of a computer program having computer-readable instructions that are executable to perform the method of the embodiment. However, in other embodiments, the various circuitries may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

The data processing apparatus 10 of FIG. 1 is configured to perform methods as illustrated and/or described in the following. It is a feature of the present embodiment that the image augmentation circuitry 100 is able to perform an augmentation process on a medical image, based on, for example, probability information relating to a location in an anatomical region for a feature of interest. The feature of interest may be, for example, a lesion or a type of lesion, artefact or pathology or any other pertinent feature. The feature of interest may also be referred to, in the following, as an augmentation feature. In some embodiments, the artefacts include any artefact found in medical image data, for example, clips, stents, or any artefact found in medical image data.

It has been found that for some type of lesions, their location and appearance is neither random nor equiprobable in tissue. For example, brain hemorrhage subtype like intraventricular or subdural is strongly linked to the location in the brain and augmentation. Therefore, image augmentation in which the lesion is pasted randomly in the brain may prove unsuccessful, for example, for the purposes of instance segmentation. Embodiments described in the following relate to an image augmentation method that combines anatomical knowledge of the location of lesions, for example, knowledge of location depending on their subtype and tissue anatomy. The embodiments described in the following relate to generating new volumes with lesions using anatomical knowledge represented by probability information for a location. In the described embodiments, the probability information is represented by a probability density map.

The described embodiments also relate to the observation that some patients can present multiple pathologies and thus their data may include multiple artefacts. It may be useful to perform image augmentation processes using only a subset of those lesions/pathologies, while still respecting anatomical constraints. As an example, such a constraint may relate to the inpainting procedure, such as preventing inpainting of a ventricle with image data coming from white matter. Knowledge acquired from healthy tissue anatomy and appearance represented by atlases or other reference images, as well as any knowledge of symmetry of the considered tissue may be used. The described embodiments may also address the observation that due to anatomical constraints lesions may have to be transformed to fit the local anatomy.

Figure 2:
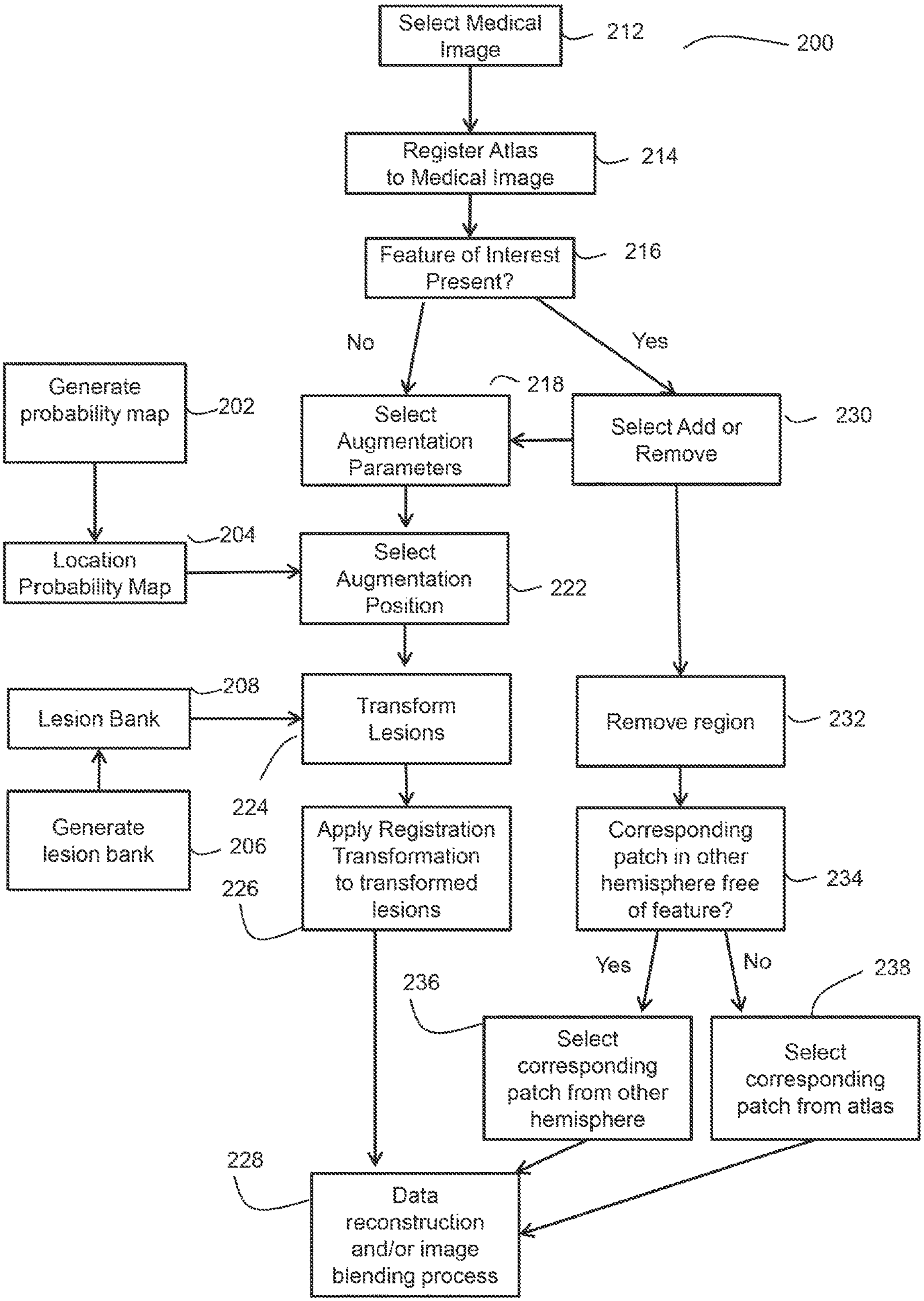
FIG. 2 is a flowchart illustrating the steps of an image augmentation process of an embodiment.

FIG. 2 is a flow-chart depicting a method 200 for performing an image augmentation process on medical image to generate an augmented image. The image augmentation process may form part of a process for generating annotated training data, for example, for use in training a machine learning procedure. The image augmentation process includes image augmentation operations such as removing and/or adding features of interest to medical images. The image augmentation depends on using pre-determined knowledge of anatomical location for a particular feature of interest in an anatomical region to generate new annotated images. In particular, the knowledge can be represented by probability information, in the form of a location probability map.

As an initial step, a number of medical images are obtained. The medical images are images of an anatomical region of interest. In the present embodiment, the anatomical region of interest is the brain region and the medical images are images representative of a view of the brain. In the present embodiment, the features of interest are lesions and may be one of a number of different types of lesion. The feature of interest can include any lesion that has a location component. Some of the medical images used to generate the probability map have one or more lesions present and some of the medical images are free of lesions. In some embodiments, the medical images correspond to one or more tissue volumes.

While the described embodiments relate to images of brains, it will be understood that other types of medical image, for example, medical images corresponding to views of different types of anatomical regions may be used. Furthermore, the feature of interest, also referred to as an augmentation feature, may include different types of lesion types, artefacts and/or pathologies. In the present embodiment, the images processed plurality of images include images of the same modality, in the present embodiment, these are CT scan images. It will be understood that images from other types of modalities may be used in other embodiments.

As an initial step, an information extraction process is performed. The information extracting process includes processing the obtained medical images to determine probability information associated with a feature of interest. The probability information includes, at least, probability information for a location of the feature of interest.

At step 202, probability information for a location of the lesion is determined. In the present embodiment, at step 202, a location probability map 204 for every subtype of lesion is generated.

In the present embodiment, the probability map is generated by registering each image to an anatomical atlas. The location of the lesion or other feature of interest in the registered brain is then determined and used to build the probability map. The registration process may be performed using a number of different, known registration procedures. It will be understood that different combinations of registration procedures and algorithms. The most suitable combination of registration algorithms may depend on a number of factors for example, the type of tissue, the type of lesion and the image modality. The result of the registration process is that the position of the objects in the image are defined with reference to a set of co-ordinates or frame of reference.

For each image, an instance of the feature of interest is identified using one or more known object identification algorithms and location data representative of the location of the lesion in the brain region is obtained. In the present embodiment, the type of lesion is also identified at this stage.

In other embodiments, the type of lesion is pre-determined, for example, while generating the lesion bank, and provided as an input at this stage. It will be understood that a number of object identification and/or image segmentation procedures may be used to identify the feature of interest for the particular type of image and the feature of interest. In some embodiments, manually or semi-automatically obtained masks (for example, masks, rough annotations or bounding boxes) can be used. These may be implemented at this stage of the method or at an initial stage of the method. The type of object identification or image segmentation procedure may be selected in dependence on, for example, the image modality, tissue and type of lesion or feature of interest.

For each type of identified lesion in the number of images, the corresponding locations in the brain region are combined to create a location probability density map for that type of identified lesion. The location probability density map can be represented as a function of position across an image. The location probability density map is therefore dependent on a position in the map, in that each position in the generated map has a value of probability density. The extracted probability information is therefore representative of a spatial probability distribution across the anatomical region. In the present embodiment, the image data used to determine the location probability map is three dimensional scan data and therefore the location probability map is determined in three spatial dimensions. It will be understood that in embodiments in which the scan data is two dimensional, the location probability map is a spatial probability distribution in two dimensions.

In some embodiments, each pixel of the map has an assigned probability value. In some embodiments, the map may be partitioned into smaller partitions and each partition may be assigned a probability value.

By generating the location probability density maps for each lesion subtype, the location probability density maps represent anatomical information about the most likely location of a lesion subtype derived by processing the number of medical images. Location and/or anatomical information for each subtype of lesion is therefore obtained by image data processing and, in the present embodiment, represented by the location probability density information map. The location probability maps therefore represents pre-determined anatomical information and/or knowledge about the most likely location of a lesion subtype.

In some embodiments, the location probability map is referred to as a positional probability map. In some embodiment, the location probability map comprises an anatomical atlas that is mapped to an existence probability of a pre-determined lesion. For example, the location probability map may correspond to a probability that a lesion exists at a particular position in the anatomical atlas.

At step 206, a lesion bank 208 is generated. The lesion bank may also be referred to as a reference image data store and includes data representing one or more reference images for each subtype of lesion. The reference images are used as a source of image data, for example to provide image patches for augmenting specific lesions of interest. Each reference images are registered to an atlas, which allows a geometrical mapping to be determined between the reference image and image to be augmented, as described in the following. In the present embodiment, the reference images are in the same modality. The reference images, for example of the brain, are registered to an atlas so that they the reference images are in a common reference space or co-ordinate system. The common reference allows the probability maps to be built. In addition, the registration to the atlas allows the determination of a geometrical mapping between the atlas and the image to be augmented that is sufficient to obtain the correct transformation and allowing inpainting of a new lesion on the image to be augmented.

In the present embodiment, a cropping process is performed so that the stored image data represent a part of the processed image, in particular, a part that includes the feature of interest. For example, in the present embodiment, the image data stored in the lesion bank represents the lesion rather than the entire brain region. In some embodiments, the lesion bank is a store of data representing reference lesion patches.

The generated location probability map is stored in a probability map store. This may correspond to or be part of data store 106. Likewise, the data of the lesion bank is stored, for example, in data store 106. In some embodiments, it will be understood that the location probability map and the data of the lesion bank are stored separately (for example, on different storage resources and/or at different storage locations on a network).

It will be understood that, in some embodiments, that steps 202 and 206 may at least partially overlap, in that at least part of the lesion bank may be generated during the image processing steps for generating the probability map.

At step 212, an image of the number of medical images is selected for augmentation. In the present embodiment, the image to be augmented is selected based on for example, a specific selection criteria, a specific image or as part of a random process from the number of medical images and may be referred to as an image to be augmented. In some embodiments, step 212 includes receiving user input data representing a specific selection criteria from the user. In some embodiments, a number of images are displayed to the user, and step 212 involves or representing a selection of a specific image. Images that do not have any augmentation features may be referred to as exemplar images.

At step 214, a registration of the image of the brain to an atlas is performed. This step can be performed in accordance with a number of known registration procedures. In the present embodiment, the registration of the brain is a deformable registration. The deformable registration procedure includes a combination of affine and demon based registration algorithms to account for the variations of anatomy and lesions between a particular brain and the atlas.

At step 216, a process of determining that the image to be augmented is representative of an image with or an image without a lesion is performed. If the brain image is identified as a healthy brain (i.e. the feature of interest, the lesion, is absent) then the method continues to step 218. If the brain image is identified as non-healthy, (i.e. one or more lesions are present) then the method continues to step 230.

The determining of the present and/or absence of the feature of interest in the lesion may be performed either manually, semi-automatically or using known object detection and/or image segmentation algorithms. In some embodiments, the presence and/or absence and/or other characteristics of the image to be augmented is obtained during a pre-processing stage, for example, during the further information extraction step and these characteristics are retrieved when the medical image is selected at step 212.

At step 218, a number of augmentation feature parameters are selected for adding of the feature of interest. An example of augmenting a medical image by adding a feature of interest is described, for example, with reference to FIG. 5. The augmentation feature parameters selected at this step include the type of the augmentation feature. In the present embodiment, the type of augmentation feature corresponds to the type and/or sub-type of lesion. The augmentation feature parameters also include the number of features of interest to be added. The augmentation feature parameters can also include, as an example, the scale of the lesion to be augmented into the selected image. The augmentation feature parameters may also include parameters representing a geometrical or intensity based deformation. In the present embodiment, the augmentation feature parameters are selected in accordance with a random process.

At step 222, augmentation operation of adding a lesion to an image is performed. In such an operation, the position in the image at which the lesion is to be added may be referred to an augmentation position. At step 222, for the type of feature of interest selected at step 218, the augmentation position in the image to be augmented is determined using the location probability map for the selected type of feature. The augmentation position may also be referred to, as the inpainting position.

It will be understood that different positioning methods may be used to select the augmentation position based on a location probability map and/or pre-determined probability information for the location. In some embodiments, the augmentation position is calculated using a global positioning method. Such global positioning may be combined with adjustment to the local anatomy using either manual, rigid, or non-rigid registration or any combination of these.

At step 224, a lesion transformation process is performed to produce a transformed lesion. Firstly, a reference image of the lesion type or a reference lesion patch is obtained from the lesion bank 210. Secondly, a transformation process is then performed to transform the obtained image data to fit to the image to be augmented. The transformation process can include a number of different transformation operations. Step 224 outputs transformed image data representing a transformed lesion. The transformation steps include, for example, one or more image transformation steps such as a change in orientation, rotation, flip, crop, resize, resample, normalization, elastic deformation.

At step 224, a transformation is made to position the lesion at its destination according to the location probability map, the adjustment to local anatomy and any local geometrical or intensity based transformations that are applied to the lesion. This is done in the co-ordinate space of the atlas.

In some embodiments, a predetermined rule is retrieved from storage for data augmentation and data augmentation process and/or augmentation position is based on the rule. In some embodiments, the rule is based on anatomical information and/or knowledge. For example, the rule may be based on pre-determined probability information, for example, a location probability map that represents or is based on anatomical information and/or knowledge.

Following the transformation at step 224, the registration previously computed in step 214 is used to transfer the transformed and positioned lesion onto the image to be augmented so that it can be inpainted, as described with reference to step 226. In further detail, at step 226, registration transformations are applied to the transformed lesions. In further detail, at step 226, a geometrical mapping is determined between the image to be augmented and the reference image and then applied to the transformed lesion. The application of the geometrical mapping to the transformed lesion transfers the chosen augmentation feature into the augmentation position in the image to be augmented.

It will be understood that, while the method includes separate steps 214 and 226, in some embodiments, the geometrical mapping used at step 226 is determined based on the registration performed at an earlier stage, for example, at step 214. In some embodiments, the geometrical mapping is determined at step 214. In some embodiments, if the references images that are used to create the location probability maps and the lesion banks are excluded then only a single registration performed during the process: from the atlas to the image to be augmented. The geometrical mapping determined at step 214 is then used to transfer the lesion from the atlas space to the image space in step 226.

In some embodiments, the transformation and geometrical mapping of steps 224 and 226 uses knowledge of the local anatomy of the image to be augmented. In particular, the transformation used information from the target image that is local to the selected augmentation position. For example, a subdural hemorrhage taken from the left side of the brain will be appropriately rotated when inpainted on the right side of it to fit local brain and skull curvature. The transformation may therefore take into account anatomical constraints in the image to be augmented.

As a non-limiting example, in the present embodiment, a brain can be approximated as a circular shape and the centre of the circular shape can be determined and used as the centre of a transformation. In such an example, a new position and orientation can be determined based on the computation of the affine transformation between the centre of the lesion and the augmentation position using the centre of the brain as the centre of the in-plane rotation used in the transformation. Such a transformation provides the correct orientation and positioning for the lesion in the image to be augmented. It will be understood that, for other tissues in which a circular shape approximation is not appropriate, alternative transformations may be determined.

The determination of the augmentation position and the transformation may be dependent on context. In the case of brain images, as described above, the determination of the augmentation position is performed based on the corresponding probability map. In some embodiments, the determination of the augmentation position may include a first determination of a position and a further adjustment to the augmentation position, for example, as part of the geometrical mapping. In some embodiments, an augmentation position corresponds to a global position and is determined based on the probability map to give a general location or a region in which to augment the lesion and then a local adjustment to the augmentation position is then determined based on, for example, the target anatomy or the transformation applied to the lesion.

As a non-limiting example, an augmentation position may be determined in the left hemisphere of the brain image. The method may include determining a transformation of the lesion based on the image to be augmented, in this example, a re-orientation of the image. A geometrical mapping is then determined for mapping the re-oriented lesion to the image to be augmented, taking into account the initial augmentation position, the re-orientation of the lesion and the image to be augmented.

In addition to transformations based on a geometrical mapping, transformations in the form of image distortions may be applied to the lesion image data. The distortions can be a combination of different types of distortion, for example, geometrical and/or appearance distortions. These distortions can be performed based on properties of the image to be augmented, the target anatomical region or the type and/or other property of the feature of interest.

While steps 222, 224, 226 are described above as separate steps, it will be understood that one or more parts of these steps may be combined.

At step 228, an image data reconstruction and/or image blending process is performed to the transformed lesion to match the lesion to the image. Any suitable image blending and/or image data reconstruction procedure can be used at step 228 to match the added lesion to the local background of the image. In the present embodiment, an image inpainting process is performed to add the transformed lesion to the image at the calculated augmentation position, thereby to produce the augmented image. In the present embodiment, the inpainting process is a Poisson blending based procedure. In the present embodiment, the inpainting method is applied to a neighbourhood about the selected augmentation position in the image.

As described above, if one or more features of interest are present in the image at step 216, then the method continues to step 230. At step 230, it is determined whether to remove a feature of interest or to add a further feature of interest. In the present embodiment, this step may be performed randomly, however, in some embodiments this step may be performed in accordance with, for example, a weighted random process based on, for example, lesion number information derived by processing the number of medical images.

If it is determined that a further lesion should be added, then the method continues to step 218, as described above. If it is determined that a lesion should be removed from the image to be augmented, the method continues to step 232. As described in the following, the augmentation operation of removal of a lesion is combined with reconstruction of the removed part of the image. As described in the following, the reconstruction process, in the present embodiment, an inpainting process, uses anatomical information coming from either knowledge of a symmetry in the tissue or an atlas. An example of augmenting a medical image by removal of a feature of interest, in accordance with the present embodiment, is described with reference to FIGS. 3 and 4.

At step 232, a part or region of the image that includes the identified lesion is selected and then removed by cropping from the image to be augmented. The part or region of the image is referred to, in the following, as a patch. Following removal, the image to be augmented has a removed patch corresponding to a part of the image that is absent any image data in place of the identified lesion.

Following removal of the identified lesion, a patch reconstruction process is performed by inpainting or infilling the removed patch. In the present embodiment, the region inpainting process uses image data from a reference patch for example, the region infilling process uses image data representing a lesion-free patch of a further reference image, for example, an atlas, or a lesion-free patch of the selected image. In some embodiments, for a lesion-free patch for both the reference image or for the atlas, the selected reference patch is anatomically equivalent to the corresponding patch that is being inpainted. For example, for a patch to be inpainted, the reference patch may be at the corresponding position in the region of interest in the reference image or at a corresponding position in the opposite hemisphere. A number of known inpainting procedures use random patches from all over the image or the dataset or from neighbouring patches to the one that is inpainted area used. In the present embodiment, the patches in the reference image that are used for obtaining image data are constrained to be those that are anatomically relevant.

As part of the region inpainting process, at step 234, it is determined if there is a corresponding part of the image from which image data can be used for the inpainting process. In the present embodiment, the determination is based on determining whether there is a corresponding patch in the other hemisphere of the brain that is free of the lesions. In this determination step, symmetry information is used to generate the anatomically realistic volumes. Information provided by one or more tissue atlases may also be used for inpainting. In some embodiments, the patch is selected based on a spatial relationship between the patch that is removed and the patch of the image or a reference image. For example, in some embodiments, for a reference image, an image patch at a corresponding location in the reference image is selected.

If it is determined that the corresponding patch in the other hemisphere is free from lesion (no lesion is present in the corresponding patch) then that patch is selected and the image data from that corresponding patch is used for the inpainting process. In further detail, the method process to step 236. At step 236 the corresponding patch is selected and used to fill the region removed at step 232.

If it is determined, that the corresponding patch in the other hemisphere is not free from lesion (lesion present in corresponding patch) then the method proceeds to step 238. At step 238, image data from a reference image is used for the infilling process. In the present embodiment, the method uses an atlas and step 238 includes selecting a corresponding patch in the atlas and extracting the image data from the selected corresponding patch for inpainting.

The method proceeds to step 228, as described above to perform the image data reconstruction and/or blending process, for example, an inpainting process. As described above, the inpainting process can be any suitable image reconstruction process. The image data reconstruction process and/or image blending process is performed in accordance with one or more known procedures or algorithms. In some embodiments, the procedure is selected based on, for example, at least one of a modality and/or a type of the feature of interest and/or an anatomical location.

In the present embodiment, as a final step, the generated augmented images are annotated with annotation data. In the present embodiment, the annotation data includes, for example, the type of the feature of interest. The generated augmented and annotated images are then stored for use, for example, in a training process for training a machine learning procedure. Every lesion that is stored in the lesion bank is associated with annotation data, including data representing the type of the lesion. In the present embodiment, a probability map is stored for each type of lesion and therefore there is a probability map for each annotation type. Therefore, the annotation type of the lesion that is being added can be used to guide which location probability map to use and will be used to annotate the augmented image.

Figure 3:
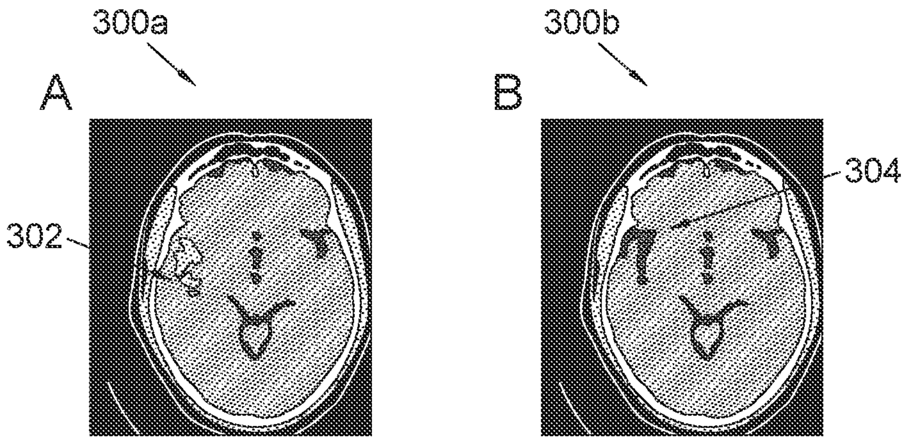
FIG. 3 is a first illustration of a medical image depicting a view of a human brain before and after an image augmentation process.

FIG. 3 shows an example of a medical image before an augmentation process (medical image to be augmented 300*a*) and a medical image resulting from the augmentation process (augmented image 300*b*). The augmentation process is performed as described with reference to FIG. 2. The medical image 300*a* is a CT scan image of brain. The medical image 300*a* has a lesion portion 302 at which a lesion is present.

The augmented image 300*b* depicts the medical image 300*a* after an augmentation process. As can be observed, in this example, the augmentation process includes the augmentation operation of removing the portion of the medical image 300*a* including the lesion 302 to form a removed patch. An inpainting process is then performed on the removed patch to from an inpainted patch 304, as described with reference to FIG. 2. The produced augmented image 300*b* is an image representing a brain without the lesion.

Figure 4:
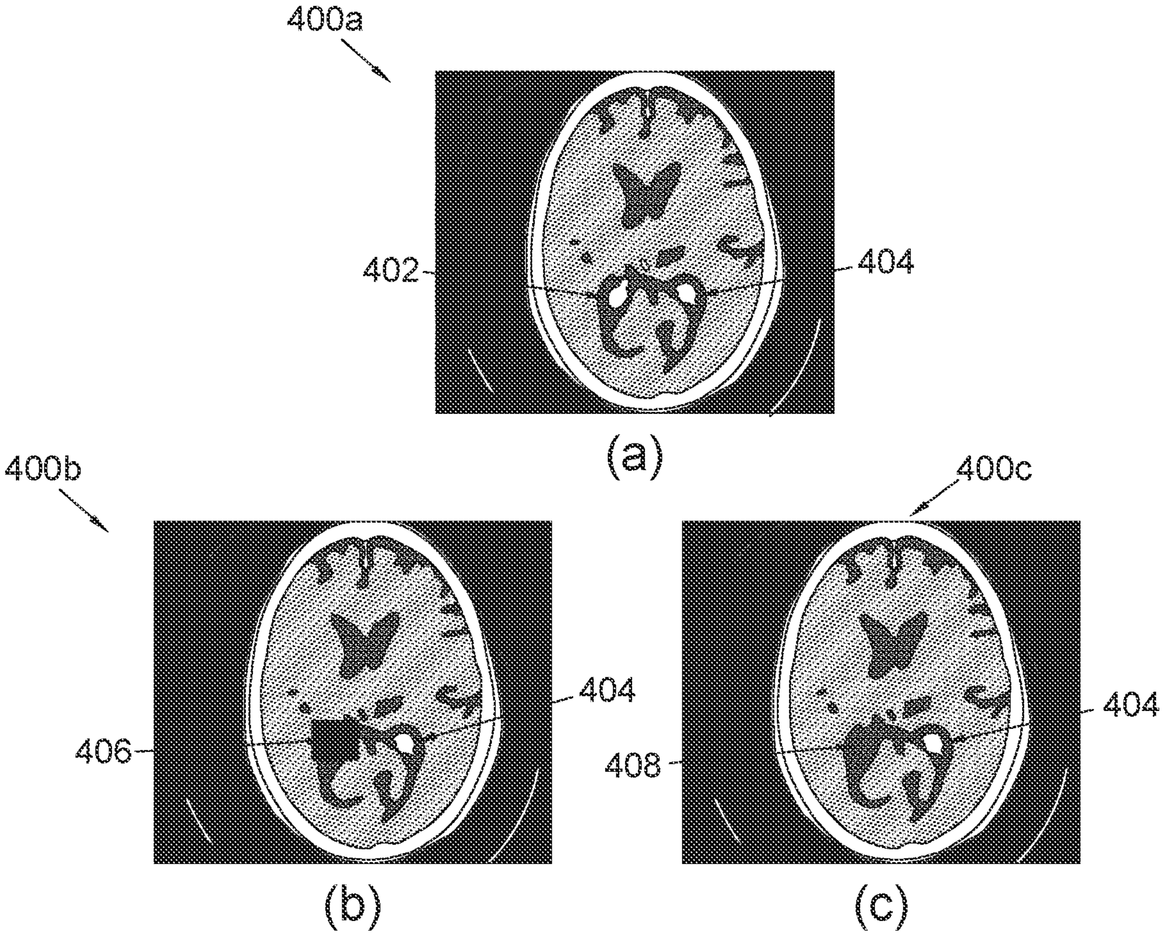
FIG. 4 is a second illustration of a medical image depicting a view of a human brain before and after an image augmentation process.

FIG. 4 shows an example of an image augmentation process. FIG. 4(*a*) shows an example medical image 400*a*; FIG. 4(*b*) shows an intermediate augmented image 400*b*, and FIG. 4(*c*) shows a final augmented image 400*c*.

FIG. 4(*a*) shows medical image 400*a* which is an image of a brain with two intraventricular hemorrhage lesions, referred to as first lesion 402 and second lesion 404. FIG. 4(*b*) shows medical image 400*b*.

Medical image 400*b* corresponds to image 400*a* with a patch surrounding and including the first lesion 402 removed. Medical image 400*b* thus has a removed patch 406 at the location of the first lesion 402. Second lesion 404 is not removed and is present in medical image 400*b*.

FIG. 4(*c*) shows medical image 400*c*. Medical image 400*c* corresponds to the image 400*b* with the removed patch 406 inpainted to form inpainted patch 408. In this example, because the corresponding ventricle also contains a lesion (lesion 404), the removed region 406 is inpainted using information from a reference image, in this example, an atlas rather than using information from the image 400*a* itself.

The new inpainted region 408 reflects the anatomy of the atlas at that same location in the brain. The inpainting procedure uses a Poisson blending procedure so that the blending is based on local gradients and not voxel values. The Poisson blending allows the appearance of the inpainted region to match the target image. Poisson blending can be considered as an example of a local blending procedure. In the present embodiment, an inpainting procedure based on Poisson blending is used, but other image data reconstruction and/or blending procedures may be used.

Figure 5:
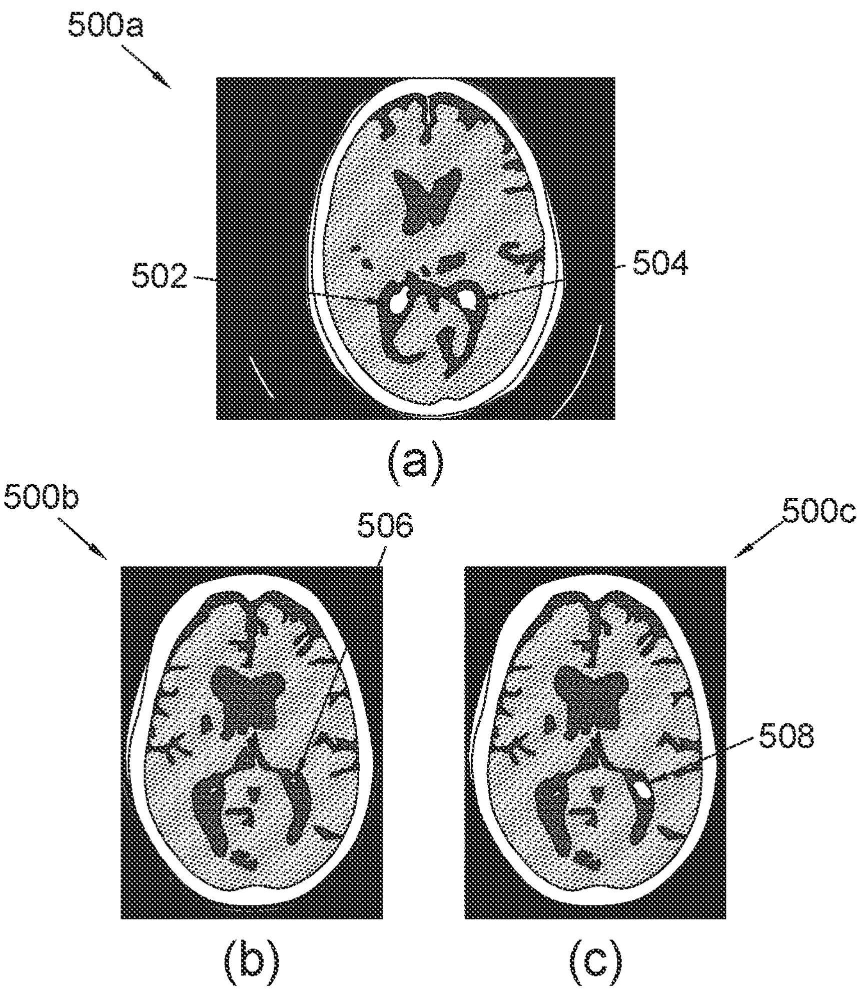
FIG. 5 is a third illustration of a medical image depicting a view of human brain before and after image augmentation.

FIG. 5 shows an example of a further image augmentation process. FIG. 5(*a*) shows a first medical image 500*a*; FIG. 5(*b*) shows a second medical image 500*b* and FIG. 5(*c*) shows a third medical image. First medical image 500*a* is an image of a first brain from which a lesion region is to be removed. Second medical image 500*b* and third medical image 500*c* are images of a second brain, before and after an augmentation process.

FIG. 5(*a*) shows the medical image 500*a* of the first brain with a first lesion 502 and a second lesion 504. The lesions are intraventricular hemorrhages lesions. Second lesion 504 is the feature of interest to be extracted from first medical image 500*a* and augmented to a further image. The first medical image 500*a* may be referred to as a reference image.

FIG. 5(*b*) shows second medical image 500*b* corresponding to the image to be augmented. The second image 500*b* is an image of a second brain before augmentation. Medical image 502*a* is an image to be augmented with the feature of interest extracted from the first medical image 500*a*.

FIG. 5(*c*) shows third medical image 500*c*. Third medical image 500*c* is an image of the second brain after an augmentation operation. The third medical image has a transformed second lesion 504 inpainted at the augmentation position to form the inpainted patch 508. The inpainting is based on Poisson Blending. By using a Poisson Blending based procedure, the lesion of the inpainted patch 508 may not appear to be exactly as it appears in medical image 500*a*.

In some embodiments, the inpainting of the lesion is performed using Poisson blending which is based on local gradients and does not directly use voxel values. The use of Poisson blending may imply that the lesion will be different in appearance from the original one and additional Gaussian blurring may not be required to avoid overfitting, during a subsequent training process, on specific lesions.

In the above-described embodiments, a method for augmenting images is described. It will be understood that the augmented images may be used for training a machine learning procedure. In further embodiments, the method may further comprises using the augmented images for the purposes of training a machine learning model and/or procedure. The above-described embodiments may also be used to increase generalization while reducing transfer gap between different datasets.

In the above-described embodiments, a lesion bank formed from a dataset was described that stores image data representing the appearances of different lesions from different datasets. It will be understood that these image data may be created from more than one dataset.

In the above-described embodiments, in particular, in the FIGS. 3 to 5, non-overlapping lesions are depicted. In some embodiments, it will be understood that one or more augmentation features may overlap. In some embodiments, for the case in which the features do not overlap, the possible locations in the location probability maps are restricted to locations where there is no lesion present.

As described above, the augmentation operation to be performed may be selected at random. In some embodiments, where more than one feature of interest is identified in the brain region, the selection of the feature of interest to be removed may be performed at random, or selected based on, one or more of the location of the feature of interest or the type of the feature of interest removal. In some embodiments, the choice of augmentation operation is manually selected, for example, based on user input.

In the above-described embodiment, the augmentation feature parameters representing further properties of the augmentation feature (including size and/or scale and/or type of feature of interest) were described as selected at random. In some embodiments, information collected for a further property of the feature of interest is collected and used to during the selection of one or more of these parameters. For example, this information may be collected at step 202 or step 206. As a non-limiting example, when generating the lesion bank and/or the location probability map, size information for each type of lesion may be collected. This size information may then be used when selecting the size parameter for augmentation. For example, the size information may relate to a permitted range of sizes for the feature, based on the determined sized by processing the number of medical images. As a further example, in some embodiments, a probability distribution that varies over permitted sizes may be generated and used for selection of the size. Likewise, in some embodiments, the number of lesions to be added may be selected using lesion number information derived from the number of medical images, for example, using a probability distribution. As a further example, certain types of feature of interest may be more probable than other types in an anatomical region and probability information related to the type of feature may be collected and then used to select the type of feature.

In further embodiments, one or more of the augmentation feature parameters may be selected manually by a user, for example, by a user providing user input representing their selection.

Whilst particular circuitries have been described herein, in alternative embodiments, functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical imaging system, comprising:

a data storage resource configured to store probability data representing probability information for a location of at least one feature of interest in an anatomical region; and processing circuitry configured to:

receive medical image data representing a medical image of the anatomical region;

determine a presence of a particular feature of interest by processing the received medical image data;

retrieve the probability data from the data storage resource; and process the medical image data to perform at least one image augmentation operation on the medical image represented by the received medical image data for the particular feature of interest, wherein the at least one image augmentation operation comprises:

removing the particular feature of interest from the medical image to form a removed patch and performing an image data reconstruction process on the removed patch using image data obtained from a further patch of the medical image or image data from a reference patch of a reference image, wherein the further patch or the reference patch is selected based on a spatial relationship between the removed patch and the further patch or the reference patch, and/or is based on symmetry information of the anatomical region, wherein the image data reconstruction process includes a region inpainting process of inpainting the removed patch, and the region inpainting process uses image data representing a lesion-free patch of the medical image or a lesion-free patch of the reference image to inpaint the removed patch, wherein the processing circuitry is further configured to obtain image data representative of the particular feature of interest, and perform a transformation on the obtained image data to produce a transformed feature of interest for augmenting to the medical image, and wherein the augmenting comprises adding the transformed feature of interest to the medical image based on the probability data.

2. The system of claim 1, wherein the processing circuitry is further configured to determine an augmentation position in the medical image based on the probability data for the location, and the augmentation operation comprises adding the particular feature of interest to the image at the augmentation position.

3. The system of claim 2, wherein the augmentation operation further comprises performing an image blending process for the particular feature of interest at the determined augmentation position.

4. The system of claim 3, wherein the image blending process comprises an inpainting process.

5. The system according to claim 1, wherein the particular feature of interest comprises at least one of a lesion, a pathology, or an artefact.

6. The system according to claim 1, wherein at least one of:

the probability information for the location is represented by a probability map;

the probability information is representative of a spatial probability density across the anatomical region; or the probability information is representative of anatomical information and/or anatomical knowledge of the at least one feature of interest in the anatomical region.

7. The system according to claim 1, wherein the processing circuitry is further configured to determine an augmentation feature parameter for the at least one feature of interest, wherein the augmentation feature parameter comprises at least one of size, scale, type, or subtype, wherein the augmentation feature parameter is selected using the probability information associated with the augmentation feature parameter.

8. The system according to claim 1, wherein the processing circuitry is further configured to obtain reference image data representing one or more images of at least a part of the anatomical region and determine a geometrical mapping between the part of the anatomical region and a corresponding part of the medical image; and wherein the at least one image augmentation operation is based at least one on the determined geometrical mapping.

9. The system according to claim 8, wherein at least one of:

the reference image data represents one or more anatomical atlases;

the reference image data represents one or more further reference images in the same modality;

the reference image data comprises a tissue volume or a set of tissue volumes; or the reference image data are representative of a particular part of the anatomical region that is free of the at least one feature of interest.

10. The system according to claim 1, wherein the at least one augmentation operation further comprises adding one or more features of interest to the medical image.

11. The system according to claim 1, wherein the at least one image augmentation operation comprises the image data reconstruction process and/or an image blending process, wherein the image data reconstruction process and/or the image blending process is performed in accordance with a pre-determined image data reconstruction procedure and/or an image blending procedure, selected based on at least one of a modality and/or a type of the particular feature of interest and/or an anatomical location.

12. The system of claim 11, wherein the pre-determined procedure comprises a procedure based on at least one of local blending, a Poisson blending, or other inpainting procedure.

13. The system according to claim 1, wherein the processing circuitry is further configured to perform a transformation of the medical image based on at least one of a manual, a rigid, or a non-rigid registration, or based on a plurality of landmarks.

14. The system according to claim 1, wherein the at least one image augmentation operation comprises applying one or more distortions to the particular feature of interest, wherein the one or more distortions comprise geometrical distortions or appearance distortions, or wherein the one or more distortions is based on the anatomical region, one or more properties of the medical image, a type, or a further property of the particular feature of interest.

15. The system according to claim 1, wherein the processing circuitry is further configured to determine the probability information for the location of the at least one feature of interest by processing medical image data representing a plurality of medical images of the anatomical region, wherein at least one of the plurality of medical images comprise the at least one feature of interest in the anatomical region.

16. The system according to claim 1, wherein the processing circuitry is further configured to obtain annotation data for the medical image associated with the at least one feature of interest.

17. A method of augmenting an image, the method comprising:

receiving medical image data representing a medical image of an anatomical region;

retrieving probability data from a data storage circuitry, wherein the probability data is representative of probability information for a location of at least one feature of interest in the anatomical region;

determine a presence of a particular feature of interest by processing the received medical image data; and processing the medical image data to perform at least one image augmentation operation on the medical image represented by the received medical image data for the particular feature of interest, wherein the at least one image augmentation operation comprises removing the particular feature of interest from the medical image to form a removed patch and performing an image data reconstruction process on the removed patch using image data obtained from a further patch of the medical image or image data from a reference patch of a reference image, wherein the further patch or the reference patch is selected based on a spatial relationship between the removed patch and the further patch or the reference patch, and/or is based on symmetry information of the anatomical region, wherein the image data reconstruction process includes a region inpainting process of inpainting the removed patch, and the region inpainting process uses image data representing a lesion-free patch of the medical image or a lesion-free patch of the reference image to inpaint the removed patch, wherein the method further comprises obtaining image data representative of the particular feature of interest, and performing a transformation on the obtained image data to produce a transformed feature of interest for augmenting to the medical image, and wherein the augmenting comprises adding the transformed feature of interest to the medical image based on the probability data.

18. A non-transitory computer-readable medium storing instructions that, when executed by processing circuitry, cause the processing circuitry to:

receive medical image data representing a medical image of an anatomical region;

retrieve probability data from a data storage circuitry, wherein the probability data is representative of probability information for a location of a feature of interest in the anatomical region;

determine a presence of a particular feature of interest by processing the received medical image data; and process the medical image data to perform at least one image augmentation operation on the medical image represented by the received medical image data for the particular feature of interest, wherein the at least one image augmentation operation comprises removing the particular feature of interest from the medical image to form a removed patch and performing an image data reconstruction process on the removed patch using image data obtained from a further patch of the medical image or image data from a reference patch of a reference image, wherein the further patch or the reference patch is selected based on a spatial relationship between the removed patch and the further patch or the reference patch, and/or is based on symmetry information of the anatomical region, wherein the image data reconstruction process includes a region inpainting process of inpainting the removed patch, and the region inpainting process uses image data representing a lesion-free patch of the medical image or a lesion-free patch of the reference image to inpaint the removed patch, wherein the processing circuitry is further configured to obtain image data representative of the particular feature of interest, and perform a transformation on the obtained image data to produce a transformed feature of interest for augmenting to the medical image, and wherein the augmenting comprises adding the transformed feature of interest to the medical image based on the probability data.

* * * * *